United States Patent [19]

Lee et al.

[11] Patent Number: 5,201,721
[45] Date of Patent: Apr. 13, 1993

[54] MEDICAL SAFETY NEEDLE AND METHOD

[76] Inventors: Chooi T. Lee, 1668 Weatherwood Dr., Manchester, Mo. 63021; Danny J. Edwards, 2207 N. Missouri, Springfield, Mo. 65803

[21] Appl. No.: 722,901

[22] Filed: Jun. 28, 1991

[51] Int. Cl.⁵ ............................................. A61M 5/32
[52] U.S. Cl. .................................. 604/198; 604/263
[58] Field of Search ................ 604/198, 192, 187, 263

[56] References Cited

U.S. PATENT DOCUMENTS

| | | | |
|---|---|---|---|
| 4,681,567 | 7/1987 | Masters et al. | 604/198 |
| 4,772,272 | 9/1988 | McFarland | 604/263 X |
| 4,813,940 | 3/1989 | Parry | 604/263 X |
| 4,816,022 | 3/1989 | Poncy | 604/263 X |
| 4,863,436 | 9/1989 | Glick | 604/198 |
| 4,915,701 | 4/1990 | Halkyard | 604/198 |
| 5,011,479 | 4/1991 | Le et al. | 604/198 |

*Primary Examiner*—John D. Yasko
*Attorney, Agent, or Firm*—Polster, Lieder, Woodruff & Lucchesi

[57] ABSTRACT

A medical safety needle assembly for a hypodermic syringe, catheter or the like. The assembly includes a hollow needle carried by a hub having at least one radially outwardly extending protrusion. A generally cylindrical hollow sheath is positioned telescopically around the hub for relative sliding reciprocal movement therebetween. The sheath, which is injection molded by the collapsible core method of plastic molding, includes at least one set of interconnecting grooves in which the protrusion is guided. A plurality of projections are positioned in the grooves to hold the protrusion, and thus the sheath, in particular locations relative to the hub and needle. First the needle is covered by the sheath to protect the needle prior to use; then the sheath is retracted to expose the needle for hypodermic use; and lastly, the sheath is moved to shield the needle to an even greater extent than it was prior to use to protect personnel from accidental needle sticks. An indicator on the sheath shows whether the needle has been used or tampered with. When in the final position, the sheath is locked to prevent accidental or secondary use of the needle. Also, after use, the needle and hub and protecting sheath may be removed and discarded as a unit from a syringe or other medical device. This feature allows reuse of the medical device while the discarded needle remains shielded.

21 Claims, 2 Drawing Sheets

MEDICAL SAFETY NEEDLE AND METHOD

BACKGROUND OF THE INVENTION

The present invention relates to a medical safety needle assembly for a hypodermic syringe, catheter, or the like.

Disposable hypodermic syringes, needles for intravenous tubes, and catheters are often used for administering medication and performing medical procedures such as taking blood samples from patients. Safety is a prime concern in light of the spread of body fluid transmitted diseases like AIDS, hepatitis and venereal diseases, which have greatly increased both the price and the risk of health hazards resulting from accidental punctures or "sticks" with contaminated needles. The risk is shared by doctors and hospital personnel alike. Presently, safe disposal of used syringes is a serious problem due to the possibility of accidental needle sticks and due to use of used syringes by addicts for administering illicit drugs.

Presently diabetic patients administer their medication at home. After using an insulin syringe, they recap the syringes. However, prior art caps can be easily dislocated, thus exposing the needles. While it is difficult to implement safety features on insulin syringes, the present invention has overcome this problem. As the population ages, there will be a need for increased health care. However, due to economic considerations, there may be increased pressure for treatment to be provided as out-patient. The increased use of this alternative treatment plan will require development of devices suitable for non-institutional care. Pre-sterilized disposable home-use treatment kits create a need for a safety feature to be incorporated in the design of the syringe to reduce the hazards associated with disposing of used needle devices.

In order to solve the foregoing problems, heretofore modified caps or safety sheaths have been provided that can be slid over the needle, hence eliminating the risky action of recapping the needle. Examples of prior art sheath assemblies are disclosed in U.S. Pat. Nos. 4,425,120; 4,702,738; 4,801,295; 4,915,701 and 4,917,673, the disclosures of which are incorporated herein by reference thereto.

One of the problems which lingers in prior art needle sheathing assemblies is that the assemblies are too complicated and expensive and do not permit removal and disposal of the protected needle from the medical device such as a syringe. In many prior art assemblies, specially designed syringe barrels are required to interact with the sheaths, thereby requiring additional expense in manufacture. Modification to the needle by having the locking mechanism component molded on the needle may cause potential problems. During insert molding, the needles have to be inserted into the mold. This gives rise to potential catastrophic damage to the mold if the needle is not inserted properly, or if the needle falls away from its position during the closing cycle of the mold and gets trapped between the injection mold sections. Some prior art assemblies involve modifying the barrel of the syringe to incorporate the locking mechanism. In these assemblies and the sheath includes protrusions that can attach to the locking mechanism of the barrel. It is difficult to adapt this design to other medical devices because of the bulk created by the required length of the barrel safety mechanism. Some prior assemblies have the locking mechanism exposed, allowing deactivation of the locking mechanism. Further, none of the prior assemblies have the ability to indicate whether the syringe has been tampered with or used.

The present invention is designed to solve or substantially reduce the above-described problems. An added feature of this invention is the ability to incorporate this design into existing syringes already on the market and as an add-on device to present off-the-shelf hypodermic syringes.

SUMMARY OF THE INVENTION

It is the principle object of the present invention to provide a disposable safety needle, wherein the needle can be protected before use, and wherein the needle is permanently and irreversibly concealed after use so as to avoid accidental needle sticks.

It is another object of the invention to provide a protective needle assembly which can adapt with minimum changes to existing disposable hypodermic syringes as an add-on device, and can be removed from a syringe or other appliance to allow for the disposal of the protected needle.

A further object of the invention is to provide a tamper indicator to inform the user whether the syringe has been used before or has been tampered with.

A still further object is to provide a protective needle sheath which can be formed by the collapsible mold method of injection molding.

These as well as other objects and advantages will become more apparent upon a reading of the detailed description of the preferred embodiments in conjunction with the drawings wherein:

DETAILED DESCRIPTION OF THE PREFERRED EMBODIMENTS

Figure 1:
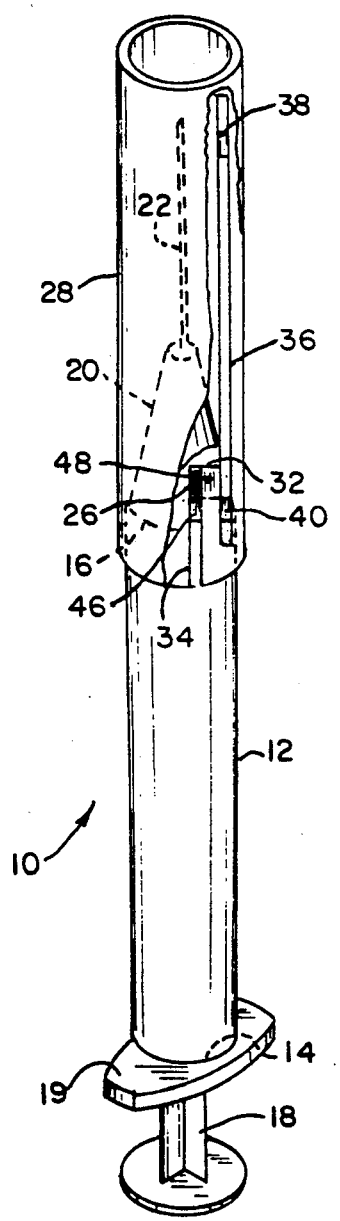
FIG. 1 is a perspective, somewhat schematic, representation of the present invention showing the protective sheath in th starting position.
Figure 2:
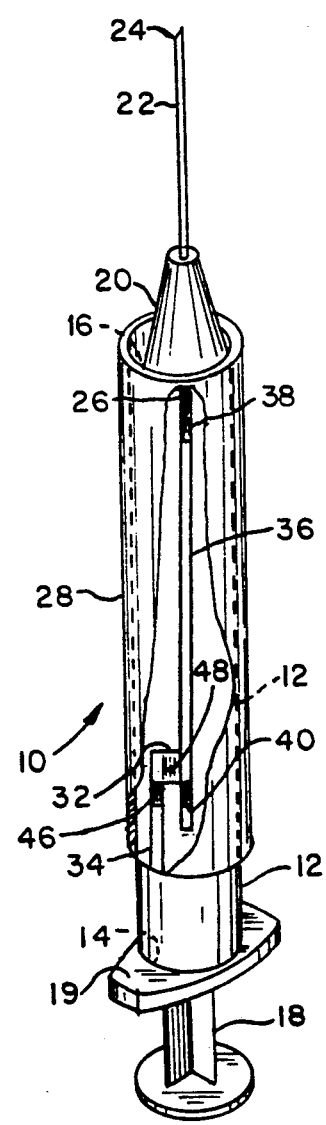
FIG. 2 is a perspective, somewhat schematic, representation of the invention showing the sheath in the retracted position.
Figure 3:
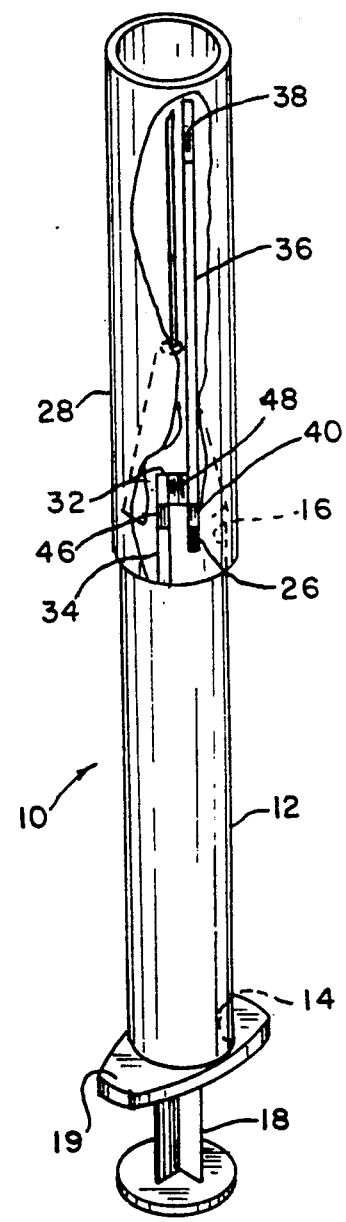
FIG. 3 is a perspective, somewhat schematic representation of the invention showing the sheath after needle use in the final locked position.

With reference to the drawings, and FIGS. 1–3 in particular, there is shown a medical hypodermic syringe generally referred to by the numeral 10, which incorporates the novel features of the present invention. It is noted at the outset that due to the advantages of the assembly according to the present invention, the invention finds equal utility on a hypodermic syringe, a catheter, an intravenous feeding tube and other similar medical devices. For purposes of clarity and brevity, the invention will be described in connection with a hypodermic syringe.

Syringe 10 may be of conventional configuration, having an elongated, generally cylindrical hollow barrel 12 having a first open end 14 and a second open end 16. A plunger 18 extends into barrel 12 through first open end 14 and includes a piston (not shown) which is adapted to draw fluid into barrel 12 when plunger 18 is drawn outwardly toward open end 14 and to expel fluid from barrel 12 when plunger 18 is pushed toward open end 16, as is conventional. Diametrically opposed ears or wings 19 permit gripping of barrel 12 by the fingers while the thumb presses on plunger 18. Adjacent open end 16 there is attached needle hub 20 carrying hollow needle 22 thereon. Needle 22 is formed with a sharpened distal end 24. As is conventional, fluid expelled out of barrel 12 by plunger 18 will travel through open end 16 and needle 22, to be injected into a patient.

Figure 5:
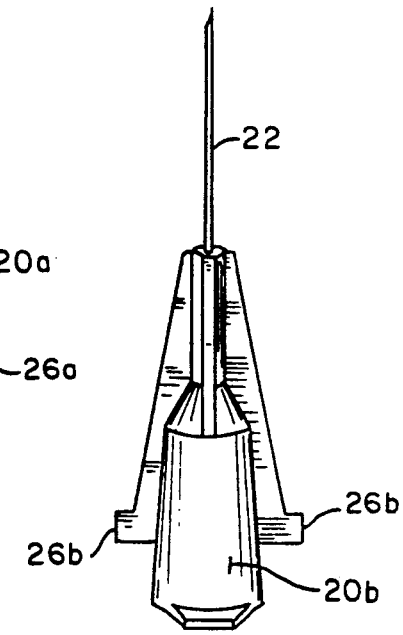
FIG. 5 is a perspective view of one preferred needle hub structure having protrusions thereon to ride in the groove set guide structure shown in FIG. 4.
Figure 6:
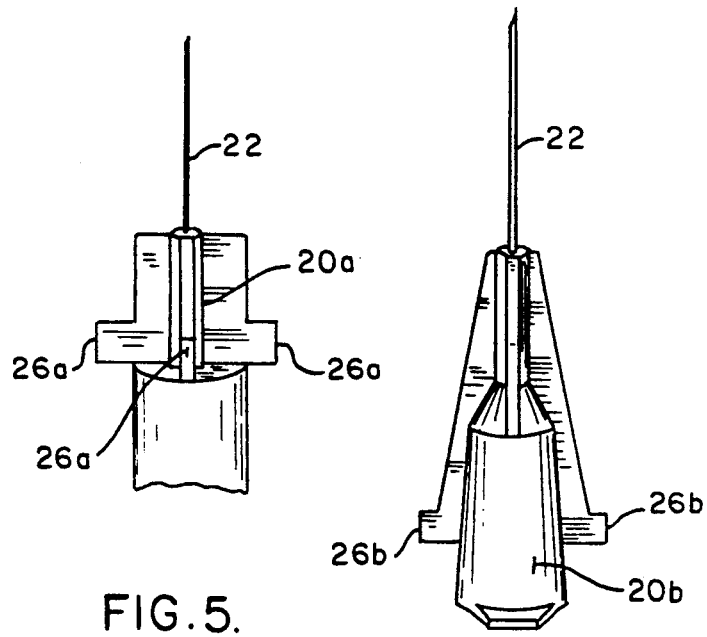
FIG. 6 is a perspective view of another preferred embodiment of needle hub structure.

Hub 20 may be of many different configurations; however, it is important that hub 20 include at least one and preferably two, three or four radially outwardly extending protrusions 26 (only one being shown for clarity). Alternative hub structures 20a and 20b are shown in FIGS. 5 and 6, respectively, showing protrusions 26a and 26b, respectively.

In order to protect needle 22 from contamination before use and to protect personnel from accidental needle sticks of a possibly contaminated needle after use, there is provided safety sheath 28. Sheath 28 is generally cylindrical and hollow, sized to telescopically reciprocate over barrel 12. It is noted that sheath 28 may slidably engage barrel 12. However, according to the principles of the present invention there is no need for sheath 28 to be in any way supported by barrel 12 as will be explained hereinafter.

Figure 4:
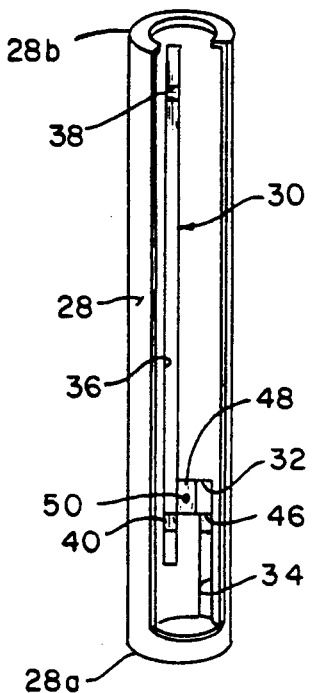
FIG. 4 is a cut-away view of the sheath per se showing a groove set guide structure.

As best seen in FIG. 4, sheath 28 has formed in the interior surface thereof a set of interconnecting grooves generally referred to by numeral 30. While only one groove set 30 is shown, it is to be understood that a plurality of identical groove sets will be provided, one groove set for each protrusion 26 of hub 20. For example, if the hub structure 20a of FIG. 5 is utilized, then four identical groove sets 30 will be utilized, spaced around the interior of sheath 28 at ninety degree intervals. If the hub structure 20b of FIG. 6 is utilized, then two identical groove sets 30 will be formed in sheath 28 spaced at one hundred eighty degrees from each other.

In the preferred embodiment, groove set 30 comprises three interconnecting grooves: a relatively short circumferentially extending starting groove 32, a relatively short longitudinally extending securing groove 34 and a relatively long longitudinally extending retracting groove 36. The width of securing groove 34 and retracting groove 36 are such that protrusion 26 may ride in and be guided by grooves 34 and 36 as sheath 28 is moved longitudinally with respect to hub 20. Securing groove 34 runs parallel to the longitudinal axis of sheath 28 and communicates between the exterior of sheath 28 at the proximal end 28a thereof and one end of starting groove 32 located about one quarter of the length of sheath 28 from proximal end 28a. Retracting groove 36 also runs parallel to the longitudinal axis of sheath 28 and securing groove 34. Retracting groove 36 extends from just short of the proximal end 28a of sheath 28 to just short of the distal end 28b of sheath 28, as best seen in FIG. 4. Retracting groove 36 is positioned to intersect with starting groove 32 at the other end thereof opposite the end intersecting with securing groove 34.

Figure 8:
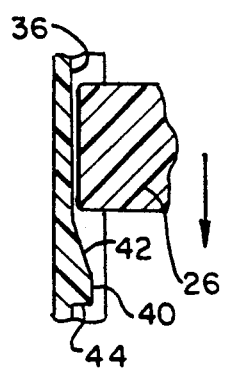
FIG. 8 is a schematic representation of a projection in a groove which allows only one-way movement of a hub protrusion thereover.
Figure 7:
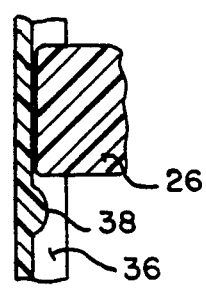
FIG. 7 is a schematic representation of a projection in a groove which allows reciprocal movement of a hub protrusion thereover.

Retracting groove 36 includes adjacent its distal end a temporary locking means comprised of a radially inwardly extending projection 38. As seen in FIG. 7, projection 38 is rounded on both sides, providing camming surfaces which allow protrusion 26 to pass thereover in both directions of longitudinal travel of protrusion 26 within retracting groove 36. Adjacent the proximal end of retracting groove 36 is a permanent locking means comprised of a radially inwardly extending projection 40. As seen in FIG. 8, projection 40 includes a camming surface 42 on one side only, allowing protrusion 26 to pass over projection 40 only in the direction of the arrow. After protrusion passes over projection 40 and the members spring back to their original shapes, protrusion 26 will be blocked by side 44 of projection 40 from moving in the direction opposite the arrow.

Securing groove 34 includes, just before the intersection of securing groove 34 and starting groove 32, a permanent locking means comprising a projection 46. Projection 46 is formed like projection 40 and permits movement of protrusion 26 only in the direction toward starting groove 32. Starting groove 32 also includes a permanent locking means comprising a radially inwardly extending projection 48 positioned between the intersection thereof with securing groove 34 and the intersection thereof with retracting groove 36. Projection 48 is similar to projection 40 and permits movement of protrusion 26 thereover only in the direction from securing groove 34 to retracting groove 36.

Syringe 10 is prepared for use in accordance with the present invention, either during manufacture or by retrofitting it with sheath 28 after purchase of a standard off-the-shelf syringe. To prepare syringe 10 for use, protrusions 26 are initially inserted into groove sets 30 through the open proximal ends of securing grooves 34. For simplicity, the operation will be described with reference to a single protrusion 26 as it is guided by a single groove set 30.

As shown in FIG. 1, protrusion 26 slides into securing groove 34 and over locking projection 46 to secure protrusion 26 in a starting position at the intersection of securing groove 34 and starting groove 32. In this starting position, sheath 28 extends beyond sharpened end 24 of needle 22 to protect the needle from contamination. Preferably a disposable cap (not shown) is placed on the distal end of sheath 28 to further protect needle 22 prior to use, or the unit is wrapped in paper during manufacture. Further, in this starting position sheath 28 is locked from longitudinal movement in either direction with respect to hub 20 and needle 22.

When syringe 10 is to be used, the optional cap is removed and sheath 28 is rotated slightly with respect to hub 20 with enough force such that protrusion 26 passes over projection 32 and into a starting position in groove 36. At this point protrusion 26 may be slid down toward the distal end of sheath 28 until it passes over temporary locking projection 38. At this point, needle 22 is exposed for use as shown in FIG. 2.

After syringe 10 has been used and needle 22 may be contaminated, sheath 28 is slid away from the user to again cover needle 22. This is accomplished by applying sufficient force to allow protrusion 26 to again pass over projection 38 in the opposite direction. Protrusion 26 then passes within retracting groove 36 until it passes over locking protrusion 40 which permanently locks protrusion 26 at the proximal end of groove 36 as shown in FIG. 3. It is noted that in this locked position sheath 28 extends further over the sharpened end 24 of needle 22 to provide even greater protection from accidental needle sticks then was the case prior to use. Also the fact that sheath 28 is locked in a different longitudinal position relative to barrel 12 than when in its starting position, acts as one indication that the syringe has been used.

Another optional method which may be employed in the present invention to indicate whether or not the medical device has been used or tampered with is to place a dot of ink 50 (FIG. 4) on projection 48 in starting groove 32. The dot of ink 50 would be easily rubbed off and the movement of protrusion 26 over projection 48 would rub off dot 50. As sheath 28 is transparent, the user could see whether or not dot 50 was present and thus know whether sheath 28 had at any time been moved from its initial starting position.

After use of the syringe 10 or other medical device with and sheath 28 extended over needle 22 as shown in FIG. 3, hub 20, needle 22 and protective sheath 28 may be removed as a unit from syringe barrel 12 or other device. Thus, needle 22 may be disposed of with the protective sheath 28 locked in place around the possibly contaminated needle.

Figure 4A:
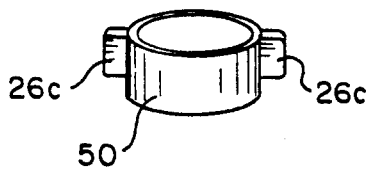
FIG. 4A is a cut-away view similar to FIG. 4, showing an alternative embodiment of the sheath.

A simplified construction of the sheath, which is used in a slightly different manner, is shown in FIG. 4A and labelled 28'. In this embodiment of the invention, the securing groove 34 and the long longitudinally extending retracting groove 36 are disposed along the same line. When using sheath 28', the syringe barrel is inserted through the opening in sheath end 28b while the needle/hub combination is held at the other end. The hub is then connected to the syringe in the conventional manner and the protrusion on the hub is inserted into groove 34. The protrusion 26 rides first in groove 34 until it passes over locking projection 46 disposed in the groove. Once protrusion 26 passes projection 46, the sheath can no longer be removed from the hub (although hub and sheath can be removed as a unit from the syringe).

In this embodiment, a two-sided projection 40, is provided in the groove set between locking projection 46 and holding projection 38. Projection 40' in this embodiment holds the sheath 28' in a the retracted position with respect to the hub until it is desired to cover the needle. Once the needle is used, sheath 28' is moved (downwardly if disposed in the position shown in FIG. 4A) until protrusion 26 passes over projection 38. At this point the needle is covered. Projection 38 in this embodiment is a locking projection, so that it locks the sheath in place over the needle.

Figure 9:
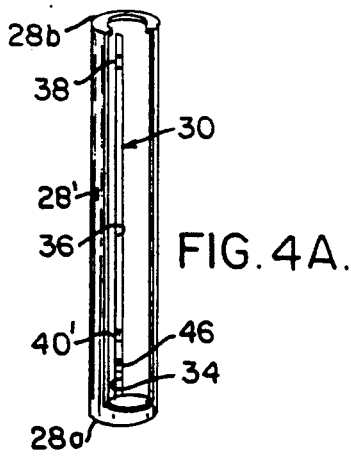
FIG. 9 is a perspective view of one add-on hub structure for adding protrusions to a medical appliance.
Figure 10:
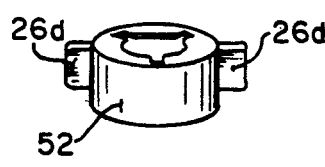
FIG. 10 is a perspective view of another add-on hub structure.

While the present invention has been shown to be operable on certain off-the-shelf syringes, it may also be adapted or retrofitted to other syringes or appliances by the addition of an adapter hub 50 (FIG. 9). Adapter hub 50 includes diametrically opposed protrusions 26C adapted to ride in groove set 30. Hub 50 may be placed on the barrel of a syringe having no other protrusions and may be attached thereto by friction fit. Alternatively, hub 50 may be attached to a barrel by induction heating or chemical, mechanical or ultrasonic means. The adapter hub 52 shown in FIG. 10 includes diametrically opposed protrusions 26d and has a central port adapted to mate with the Luer-Lok type syringe needle hub.

Sheath 28 can preferably be injection molded of transparent plastic utilizing the collapsible core method as shown and described in U.S. Pat. Nos. 3,383,460; 4,019,711; 4,383,819 and 4,533,312; the disclosures of which are incorporated herein by reference.

Having fully described the preferred forms of the invention, it can be seen that the objects and advantages of the invention have been achieved. Inasmuch as numerous modifications may be made to the preferred embodiments, described hereinabove, e.g., projection 40 may be made with two camming surfaces similar to projection 38 permitting removal of sheath 28 prior to use; such modifications do not depart from the spirit and scope of the invention. The scope of the invention is to be determined solely by the language of the following claims as interpreted in view of the Doctrine of Equivalents.

What is claimed is:

1. A safety needle comprising:
 a hollow elongated needle having a sharpened end at one end thereof;
 a hub adapted to be connected to a medical device;
 said hub including at least one radially outwardly extending protrusion;
 a generally cylindrical hollow sheath positioned telescopically around said hub for sliding reciprocal longitudinal movement with respect to said hub;
 a longitudinally extending retracting groove formed in the interior surface of said sheath sized to accept therewithin said protrusion on said hub such that said protrusion rides within said groove as said sheath is longitudinally reciprocated with respect to said hub, said retracting groove having disposed therein coming means for holding the sheath at least temporarily in one or more predetermined positions with respect to the hub;
 said sheath being movable from a first position wherein said sheath extends beyond said sharpened end for shielding said sharpened end, to a second position wherein said sheath is retracted to expose said needle for use;
 said retracting groove includes temporary locking means therein adjacent one end of said retracting groove for engaging said protrusion to hold said sheath in said second position and to release said protrusion and said sheath from said second position upon a longitudinal force being exerted on said sheath toward said needle's sharpened end;
 said temporary locking means including a radially inwardly extending projection within said retracting groove adjacent said one end of said retracting groove; and
 said projection having a camming surface on both sides thereof to allow said protrusion to pass over said projection in both direction of movement within said groove.

2. The safety needle as specified in claim 1 and further characterized by:

a circumferentially extending starting groove formed in the interior surface of said sheath extending at least partially around the interior surface of said sheath adjacent the other end of said sheath opposite said one end of said sheath and positioned longitudinally on said sheath such that when said protrusion is in said starting groove, said sheath is longitudinally located in said first position;

said starting groove being sized to accept therewithin said protrusion on said hub such that rotary movement of the sheath relative to said hub will cause said protrusion to ride within said starting groove from a starting position to said first position.

3. The safety needle as specified in claim 2 and further characterized by:

a starting projection in said starting groove between said starting position and said first position for holding said protrusion in said starting position until a rotary force is applied to said sheath relative to said hub to allow said protrusion to pass over said starting projection.

4. The safety needle as specified in claim 3 and further characterized by:

said starting projection having a camming surface on only one side thereof to prevent said protrusion from passing back from said first position to said starting position.

5. The safety needle as specified in claim 3 and further characterized by:

a final locking projection in said retracting groove adjacent the other end of said retracting groove opposite said one end of said retracting groove;

said final locking projection located closer to said other end of said retracting groove than the area of communication between said retracting groove with said starting groove, such that after needle use, said sheath may be extended toward said needle sharpened end and said final locking projection will hold said sheath in a third position wherein said sheath extends further beyond said sharpened end than when said sheath is in said first position.

6. The safety needle as specified in claim 5 and further characterized by:

said final locking projection extending radially inwardly within said groove and having a camming surface on only one side thereof to allow movement of said protrusion across said final locking projection only to said third position.

7. The safety needle as specified in claim 3 and further characterized by:

said starting projection having an indicator means for indicating whether or not said protrusion has passed over said starting projection, thus indicating whether the needle has been used or tampered with.

8. The safety needle as specified in claim 7 and further characterized by:

said indicator means includes a colored spot on said starting projection which spot will be rubbed off when said protrusion passes over said starting projection.

9. The safety needle as specified in claim 3 and further characterized by:

a securing groove formed in the interior surface of said sheath sized to accept therewithin said protrusion such that said protrusion rides within said groove as said sheath is longitudinally moved on said hub;

said securing groove communicating between the exterior of said sheath at said other end of said sheath and said starting groove at said starting position, such that said protrusion can be passed through said securing groove to said starting position when said sheath is loaded onto said hub.

10. The safety needle as specified in claim 9 and further characterized by:

a fixing projection in said securing groove for holding said protrusion in said starting position.

11. The safety needle as specified in claim 10 and further characterized by:

said fixing projection having a camming surface on only one side thereof to permit movement of said protrusion over said fixing projection only in the direction toward said starting position.

12. The safety needle as specified in claim 10 and further characterized by:

said fixing projection having a camming surface on both sides thereof to permit movement of said protrusion over said fixing projection in both directions such that said sheath may be removed from said hub before said needle is used.

13. The safety needle as specified in claim 3 and further characterized by:

said retracting groove and said starting groove being duplicated in the inside surface of said sheath at the diametrically opposed positions thereof, further including a second protrusion on said hub diametrically opposed to said at least one protrusion riding in said duplicated grooves.

14. The safety needle as specified in claim 3 and further characterized by:

said retracting, starting and said securing grooves being duplicated in the inside surface of said sheath at the diametrically opposed positions thereof, further including a second protrusion on said hub diametrically opposed to said at least one protrusion riding in said duplicated grooves.

15. A hypodermic safety syringe comprising:

a generally cylindrical, hollow syringe barrel having a first open end and a second open end;

a plunger extending into said barrel through said first open end;

a hollow elongated needle having a sharpened end at one end thereof;

a hub mounted adjacent said second open end of said barrel;

said hub including at least one radially outwardly extending protrusion;

a generally cylindrical hollow sheath positioned telescopically around said hub for sliding reciprocal longitudinal movement with respect to said hub and said syringe barrel, said sheath being sized to accept the syringe barrel and being movable reciprocably to cover at least a portion of the syringe barrel;

a longitudinal extending retracting groove formed in the interior surface of said sheath sized to accept therewithin said protrusion on said hub such that said protrusion rides within said groove as said sheath is longitudinally reciprocated with respect to said hub, said retracting groove having disposed therein camming means for holding the sheath at least temporarily in one or more predetermined positions with respect to the hub;

said sheath being movable from a first position wherein said sheath extends beyond said sharpened end for shielding said sharpened end, to a second position wherein said sheath is retracted to expose said needle for use;

said sheath being formed by the collapsible core method of injection molding.

16. A hypodermic safety syringe comprising:

a generally cylindrical, hollow syringe barrel having a first open end and a second open end;

a plunger extending into said barrel through said first open end;

a hollow elongated needle having a sharpened end at one end thereof;

a hub mounted adjacent said second open end of said barrel;

said hub including at least one radially outwardly extending protrusion;

a generally cylindrical hollow sheath positioned telescopically around said hub for sliding reciprocal longitudinal movement with respect to said hub and said syringe barrel, said sheath being sized to accept the syringe barrel and being movable reciprocably to cover at least a portion of the syringe barrel;

a longitudinally extending retracting groove formed in the interior surface of said sheath sized to accept therewithin said protrusion on said hub such that said protrusion rides within said groove as said sheath is longitudinally reciprocated with respect to said hub, said retracting groove having disposed therein camming means for holding the sheath at least temporarily in one or more predetermined positions with respect to the hub;

said sheath being movable from a first position wherein said sheath extends beyond said sharpened end for shielding said sharpened end, to a second position wherien said sheath is retracted to expose said needle for use;

said hub, said sheath and said needle being removable from such appliance as a unit while said sheath surrounds said needle and continues to protect from accidental needle sticks after said needle has been disposed of.

17. A hypodermic safety syringe comprising:

a generally cylindrical, hollow syringe barrel having a first open end and a second open end;

a plunger extending into said barrel through said first open end;

a hub mounted adjacent said second open end of said barrel, said hub carrying at least one radially outwardly extending protrusion;

a hollow needle fixed with respect to the barrel, said needle having a conduit therethrough in fluid communication through said second open end with the interior of said barrel;

said needle having a sharpened distal end:

a generally cylindrical hollow sheath positioned telescopically around said barrel for reciprocal longitudinal movement with respect to said barrel;

a longitudinally extending retracting groove formed in the interior surface of said sheath sized to accept therewithin said protrusion on said hub such that said protrusion rides within said groove as said sheath is longitudinally reciprocated with respect to said barrel;

said sheath being movable from a first position wherein said sheath extends beyond said sharpened end for shielding said sharpened end, to a second position wherein said sheath is retracted toward said first open end exposing said needle for use;

said retracting groove includes temporary locking means therein adjacent one end of said retracting groove for engaging said protrusion to hold said sheath in said second position and to release said protrusion and said sheath from said second position upon a longitudinal force being exerted on said sheath away from said barrel toward said needle sharpened end;

said temporary locking means including a radially inwardly extending projection within said retracting groove adjacent said one end of said retracting groove;

said projection having a camming surface on both sides thereof to allow said protrusion to pass over said projection in both directions of movement within said groove;

a circumferentially extending starting groove formed in the interior surface of said sheath extending at least partially around the interior surface of said sheath adjacent the other end of said sheath opposite said one end of said sheath and positioned longitudinally on said sheath such that when said protrusion is in said starting groove, said sheath is longitudinally located in said first position;

said starting groove being sized to accept therewithin said protrusion on said hub such that rotary movement of sheath relative to said barrel will cause said protrusion to ride within said starting groove from a starting position to said first position;

a starting projection in said starting groove between said starting position and said first position for holding said protrusion in said starting position until a rotary force is applied to said sheath relative to said barrel to allow said protrusion to pass over said starting projection;

a final locking projection in said retracting groove adjacent the other end of said retracting groove opposite said one end of said retracting groove; and said final locking projection being located closer to said other end of said retracting groove than the area of communication between said retracting groove with said starting groove, such that after syringe use, said sheath may be extended toward said needle sharpened end and said final locking projection will hold said sheath in a third position wherein said sheath extends further beyond said sharpened end than when said sheath is in said first position.

18. A safety needle comprising:

a hollow elongated needle having a sharpened end at one end thereof;

a hub adapted to be connected to a medical device;

said hub including at least one radially outwardly extending protrusion;

a generally cylindrical hollow sheath positioned telescopically around said hub for sliding reciprocal longitudinal movement with respect to said hub;

a longitudinally extending retracting groove formed in the interior surface of said sheath sized to accept therewithin said protrusion on said hub such that said protrusion rides within said groove as said sheath is longitudinally reciprocated with respect to said hub, said retracting groove having disposed therein camming means for holding the sheath at least temporarily in one or more predetermined positions with respect to the hub;

said sheath being movable from a first position wherein said sheath extends beyond said sharpened end for shielding said sharpened end, to a second position wherein said sheath is retracted to expose said needle for use;

said longitudinally extending retracting groove being relatively straight and extending at one end thereof to the corresponding end of the sheath to permit the protrusion on the hub to be inserted into said groove.

19. The safety needle as set forth in claim 18 wherein a locking projection is disposed in the retracting groove, which locking projection allows the hub protrusion to pass thereover in one direction to mount the sheath on the hub, but prevents movement of the hub protrusion thereover in the opposite direction to permanently secure the sheath to the hub.

20. The safety needle as set forth in claim 19 further including a syringe on which the hub is removably mounted, said sheath and hub being removable as a unit from the syringe.

21. The safety needle as set forth in claim 19 further including a second locking projection disposed at the other end of the groove whereby when the hub protrusion passes over said second locking projection the sheath is locked in place covering the needle.

* * * * *